(12) United States Patent
Eichhorst et al.

(10) Patent No.: US 8,012,133 B2
(45) Date of Patent: Sep. 6, 2011

(54) SYSTEM FOR INJECTION THROUGH OR INTO THE HUMAN SKIN

(75) Inventors: Peter Eichhorst, Hohen Neuendorf (DE); Torsten Matz, Berlin (DE); Michael Trampe, Fürstenwalde (DE)

(73) Assignee: primoJEX GmbH, Hohen Neuendorf (DE)

( * ) Notice: Subject to any disclaimer, the term of this patent is extended or adjusted under 35 U.S.C. 154(b) by 149 days.

(21) Appl. No.: 12/097,817

(22) PCT Filed: Nov. 17, 2006

(86) PCT No.: PCT/EP2006/068612
§ 371 (c)(1),
(2), (4) Date: Sep. 29, 2008

(87) PCT Pub. No.: WO2007/071510
PCT Pub. Date: Jun. 28, 2007

(65) Prior Publication Data
US 2009/0318859 A1    Dec. 24, 2009

(30) Foreign Application Priority Data

Dec. 20, 2005 (DE) .......................... 10 2005 062 220

(51) Int. Cl.
*A61M 5/31* (2006.01)
*A61M 5/30* (2006.01)
*A61M 5/00* (2006.01)

(52) U.S. Cl. .......................... 604/241; 604/68; 604/187

(58) Field of Classification Search .................. 604/68, 604/240–242, 232–233, 187–188
See application file for complete search history.

(56) References Cited

U.S. PATENT DOCUMENTS 2,147,616 A * 2/1939 Chaput .......................... 604/232
(Continued)

FOREIGN PATENT DOCUMENTS

DE    10340613 A1    3/2005
(Continued)

OTHER PUBLICATIONS

English Language Abstract for DE 10340613.
(Continued)

*Primary Examiner* — Nicholas D Lucchesi
*Assistant Examiner* — Rebecca E Eisenberg
(74) *Attorney, Agent, or Firm* — Norris McLaughlin & Marcus PC

(57) ABSTRACT

The invention relates to a system for injecting a fluid through or into the human skin, optionally by needle-free injection or by injection with a needle, with
(i) an injection device (110) which includes
an ampoule (112) with an ampoule body (114) forming a chamber for receiving the fluid to be injected;
an ampoule piston (118) which is axially movable and sealingly guided in the chamber;
an outlet (124) disposed at the distant end of the ampoule (112) for the fluid to be injected, wherein the ampoule (112) is rounded in the region of the outlet (124) and the rounded region forms a skin contact surface (126) for the needle-less injection through or into the human skin; and
at least one first coupling element (128) of a coupling device which is arranged at the distal end of the ampoule (112) on the ampoule body (114) and configured for sealingly and reversibly attaching a needle attachment (150), and
(ii) a needle attachment (150) with
a cannula part (152) comprising a needle (156); and an adapter part (154) proximally connected to the cannula part, wherein the adapter part (154) has at least one second coupling element (162) of the coupling device, the coupling device configured for sealing and reversible attachment on the ampoule (112) of the injection device (110), characterized in that the needle attachment (150) is constructed in two parts, wherein the needle attachment (150) can be reversibly disassembled into the cannula part (152) and the adapter part (154).

4 Claims, 1 Drawing Sheet

U.S. PATENT DOCUMENTS

Figure 1A:
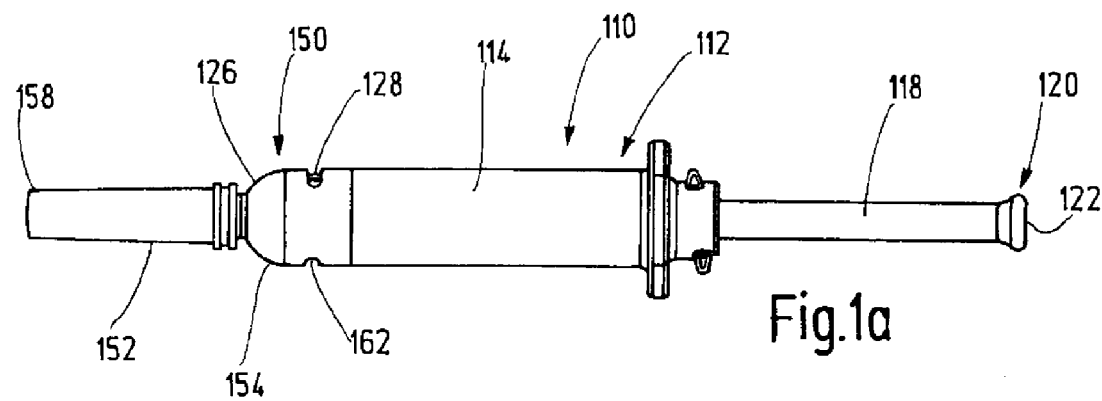

| | | | |
|---|---|---|---|
| 4,883,483 A | 11/1989 | Lindmayer | |
| 5,458,580 A * | 10/1995 | Hajishoreh | 604/240 |
| 5,919,159 A | 7/1999 | Lilley | |
| 6,077,245 A * | 6/2000 | Heinrich et al. | 604/110 |
| 6,436,076 B1 * | 8/2002 | Hsu | 604/240 |
| 2005/0192541 A1 * | 9/2005 | Novacek et al. | 604/195 |
| 2009/0124966 A1 * | 5/2009 | Oyama | 604/68 |

FOREIGN PATENT DOCUMENTS

| | | |
|---|---|---|
| DE | 102004007257 A1 | 9/2005 |

OTHER PUBLICATIONS

English Language Abstract for DE 10 2004 007257.

* cited by examiner

SYSTEM FOR INJECTION THROUGH OR INTO THE HUMAN SKIN

This application is a 371 application of PCT/EP2006/068612 filed Nov. 17, 2006, which claims priority to the German application DE 10 2005 062 220.8 filed Dec. 20, 2005.

The invention relates to a system for injecting a fluid through or into the human skin, wherein the injection can be performed either needle-free or with a needle. The invention is also directed to a needle attachment for such system which is particularly configured for the intended use of the invention.

TECHNICAL BACKGROUND AND STATE-OF-THE-ART

Various needle-less injection devices with different configurations for injecting a—typically drug-containing—fluid through or into the human skin are known in the art. The conventional devices have in common that the fluid is ejected through a very small outlet of an ampoule through application of high pressure, whereby the fluid attains a very high exit velocity which is required for penetrating the skin or entering the skin and hence for a needle-less subcutaneous or intradermal injection. Such injection devices include an ampoule with an ampoule body forming a chamber for receiving the fluid to be injected. An axially movable, sealingly guided ampoule piston is disposed inside the chamber. The distal end of the ampoule also has an outlet for the fluid to be injected. When used as indicated, the region of the ampoule surrounding the outlet defines the skin contact surface for the needle-less injection through or into the human skin.

DE 10 2004 007 257 A1 describes a needle-less injection device of the aforedescribed type wherein, in addition, an exterior shape of the distal surface of the ampoule forming the skin contact surface has a convex and essentially edge-free contour.

Injection devices employing needles have been used since many decades as an alternative to needle-less injection devices. Such injection devices have the following commonalities which are noteworthy for the intended use of the invention:
(i) an ampoule with an ampoule body forming a chamber is provided,
(ii) a movably and sealingly guided ampoule piston is disposed in the ampoule body, and
(iii) the outlet is arranged at the distal end of the ampoule, from where the fluid to be injected enters a needle and—depending on the penetration depth of the needle and the employed therapy, e.g., with intradermal, subcutaneous or intramuscular injection—is released in the patient's body.

Special embodiments of injection devices with needles are syringes with a so-called Luer connection which represents a standardized connection for injection syringes (or injection cannulae). In addition, a bayonet coupling for attaching the needle can also be provided (so-called Luer-lock syringe).

Presently, the two aforedescribed injection systems are used side-by-side; the attending physician/the medical facility providing treatment is therefore required to have both injection devices on hand, if a selection needs to be made between the two injection systems. When ampoules are pre-filled at the manufacturer with a liquid drug, a decision must already be made, if these are to be configured for needle-less injection systems or for injection systems using needles. This significantly increases material and manufacturing costs as well as inventory costs and the logistic complexity for providing both injection systems on-site.

DE 103 40 613 A1 describes a device for injecting a fluid, which can be used as a one-way syringe or—by removing certain components of the device at defined rated breakpoints—as an ampoule for a needle-less injector. However, the rated breakpoints are at risk of accidentally breaking during the needle injection. Moreover, the rated breakpoints also not sufficiently smooth to satisfy all the requirements for the needle-less injection.

U.S. Pat. No. 5,769,138 describes an adapter with Spike-attachment for a needle-less injector. The adapter and the injector each include coupling elements for securing the adapter on the injector. Additional sealing elements are provided on the adapter to prevent air from entering the chamber of the injector. U.S. Pat. No. 5,919,159 also describes an adapter with Spike-attachment for a needle-less injector.

Accordingly, there is still a great need for technical solutions which eliminate or at least alleviate the aforementioned disadvantages.

SOLUTION ACCORDING TO THE INVENTION

According to a first aspect of the invention, the object is attained by the system of the invention recited in claim 1. The invention is based on a system for injecting a fluid through or into the human skin, optionally by needle-free injection or by injection with a needle. The system includes
(i) an injection device which includes
   an ampoule with an ampoule body forming a chamber for receiving the fluid to be injected;
   an ampoule piston which is axially movable and sealingly guided in the chamber;
   an outlet disposed at the distant end of the ampoule for the fluid to be injected, wherein the ampoule is rounded in the region of the outlet and the rounded region forms a skin contact surface for the needle-less injection through or into the human skin; and
   at least one first coupling element of a coupling device which is arranged at the distal end of the ampoule on the ampoule body and configured for sealingly and reversibly attaching a needle attachment, and
(ii) a needle attachment with
   a cannula part comprising a needle; and
   an adapter part proximally connected to the cannula part, wherein the adapter part has at least one second coupling element of the coupling device, the coupling device configured for sealing and reversible attachment on the ampoule of the injection device.

The system is characterized in that the needle attachment is constructed in two parts, such that the needle attachment can be reversibly disassembled into the cannula part and the adapter part. This makes the needle attachment highly versatile; for example, a somewhat wider needle can be connected first to the adapter part for withdrawing the liquid drug from a medicine bottle which has a rubber seal, whereafter a cannula part with a needle can be selected that is optimal for the respective injection.

The invention is based on the realization that injection devices can be easily reconfigured from a needle-less configuration to a configuration for injection with a needle, and vice versa, by starting with an injection device initially configured for needle-less injection. Such injection device must then have a coupling element which engages with a complementary coupling element of a needle attachment. The two coupling elements on the injection device and on the needle attachment, respectively, thereby form a coupling device. After the injection device and needle attachment are assembled, the coupling device also guarantees a tight seal, i.e., the fluid can only exit at the tip of the needle. An important aspect of the system is that its configuration can be reversed. Depending on the situation, the user can then select, optionally several times, between the two types of injection and can therefore also more flexibly adapt to the current application situation.

In the context of the invention, the term "penetration" of the human skin is meant to indicate penetration of the fluid through the epidermis, preferably also through the corium of the skin.

For a definition of the term "rounded", reference is made to the disclosure in DE 10 2004 007 257 A1, particularly to the cross-sectional views of the ampoule bodies of FIGS. 4 to 6 and the corresponding description of these Figures, and to the disclosure in paragraph 6 of the published document. DE 10 2004 007 257 A1 describes a needle-less injection device of this general type, wherein the outer design of the distal surface of the ampoule forming the skin contact surface has a convex and essentially edge-free contour. Such contour is also referred to as rounded. For an understanding of this term, a skilled artisan will further be guided by the exemplary embodiments described below. The term "ampoule" herein includes the ampoule body and the skin contact surface, wherein the skin does not necessarily need to rest directly on the ampoule body. In the context of the invention, needles include cannulae or tubes configured as instruments for administering fluids, in particular implemented as injection cannulae.

The first coupling element is arranged on the ampoule body. The coupling element on the ampoule body is configured—depending on the design of the coupling device—to engage with a complementary coupling element disposed on the needle attachment. The coupling device is preferably a bayonet lock, because this type of lock provides a particularly secure and fluid-tight attachment.

It will be understood that the system must be fluid-tight to ensure that the device can be used for injection with a needle, so that the fluid exits only at the defined location, i.e., at the tip of the needle. To this end, corresponding sealing elements are provided which are configured to prevent the fluid from exiting between the needle attachment and the ampoule, after the needle attachment and the ampoule are joined. These sealing elements can be designed so that a surface segment of the needle attachment includes a coating made of a sealing material which is applied in a circular shape about a connection point of the needle attachment on the outlet of the ampoule; the local coated surface segment is selected so that it contacts the ampoule body after the needle attachment and the ampoule body are assembled, thereby attaining the desired sealing effect.

Alternatively or in addition, the ampoule body and the needle attachment may be manufactured in the regions, where their walls face each other after the coupling assembly has been connected, of materials having different elasticity modules, so that the softer material yields slightly when the coupling assembly is connected and thereby seals in this region. The exact geometric design of the sealing elements depends on the respective predefined geometry of the injection device and the needle attachment, respectively. A commonality exists in that a sealing action should be achieved around the region of the outlet of the ampoule to prevent the fluid from leaking out laterally between the needle attachment and the ampoule. For the actual design of the sealing elements, a skilled artisan will base his selection on sealing elements found in conventional coupling devices for fluid systems and will obtain guidance from the exemplary embodiments listed below.

A second aspect of the invention relates to a needle attachment configured for cooperation with an injection device according to the aforedescribed embodiment. The needle attachment includes a cannula part with the needle. The needle attachment further includes the adapter part connected proximal to the cannula section. The adapter part includes the at least a second coupling element of the coupling assembly, which is configured for sealing and reversible attachment to an ampoule of an injection device, wherein the first coupling element of the coupling assembly is arranged on the ampoule body of the injection device.

A third aspect of the invention relates to an adapter part which takes into account the aforedescribed two-part construction of the needle attachment. The adapter part is constructed with a Luer connection for the cannula section. Conventional needle attachments for injection systems with needles can then also be used.

Another aspect of the invention, which can be implemented independent of the above-described embodiments, relates the ampoule piston of the injection device. An end section at the proximal end of the ampoule piston is widened, forming a pressure surface for the thumb, as required for manual operation of an injection device with a needle attachment. For improved ergonomic handling, the end region should have no sharp edges and should preferably be formed with a concave inward throat (in the distal direction).

Exemplary embodiments of the invention will now be described with reference to the appended drawings.

Figure 1B:
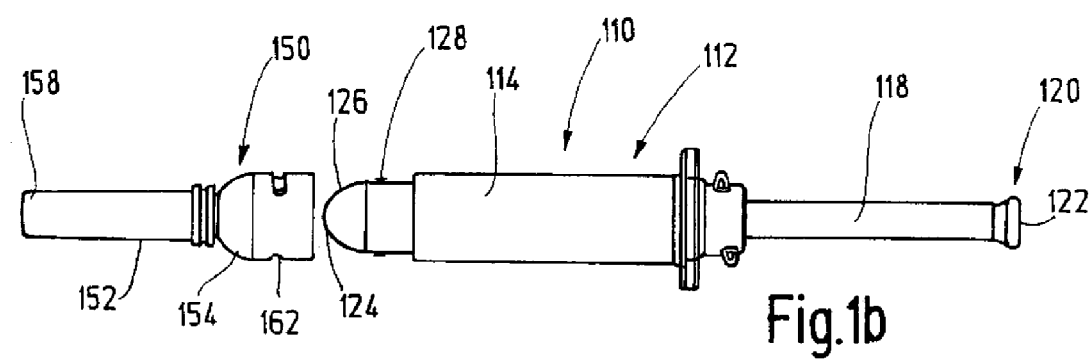
Figure 1C:
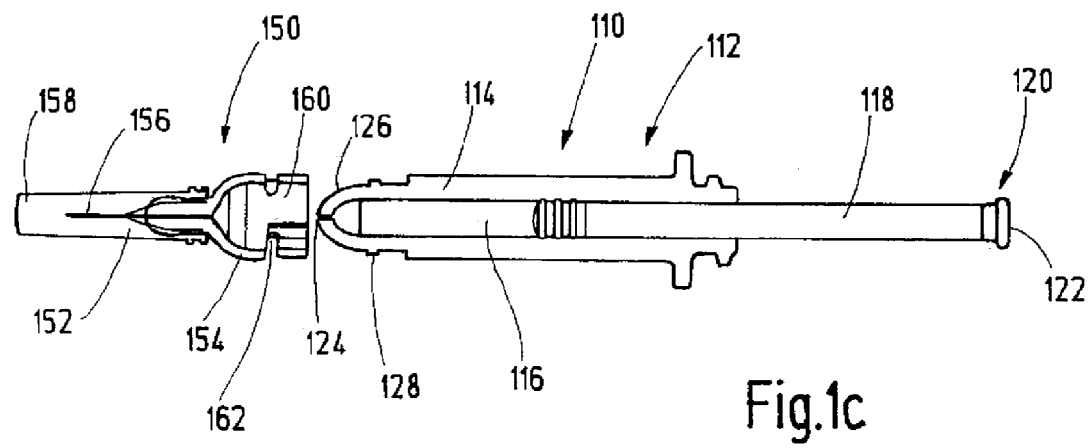
Figure 2:
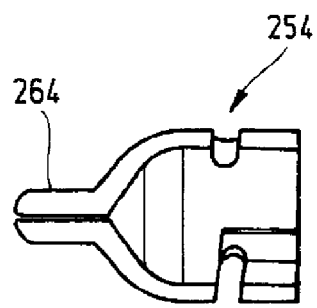

FIGS. 1a to 1c show an injection system consisting of an injection device and a corresponding needle attachment according to a first embodiment of the invention, and FIG. 2 shows an adapter part with a Luer connection as part of a two-part needle attachment according to the invention.

FIGS. 1a to 1c show—in different stages of assembly and in a schematic cross-sectional view along the longitudinal axis—a system for injecting a fluid through or into the human skin according to a first embodiment. The injection can optionally be performed needle-free or by using a needle. The system depicted in FIGS. 1a to 1c includes also an injection device 110 and a needle attachment 150.

The injection device 110 includes an ampoule 112 with an ampoule body 114 configured to receive the fluid to be injected, usually a liquid drug. The fluid is disposed in a chamber 116, inside which an axially movable and sealingly guided ampoule piston 118 is guided.

An end section 120 at the proximal end of the ampoule piston 118 is widened, thereby forming a pressure surface 122 for the thumb. To improve ergonomic handling, the end region 120 has no sharp edges and a concave inwardly trailing part. Unlike conventional syringes, the end region 120 is tapered, so that the ampoule can be inserted into the conventional injection device for needle-less injection provided for the intended use.

The injection device 110 also includes at the distal end of the ampoule 112 an outlet 124 for the fluid to be injected located. The ampoule 112 is rounded in the region of the outlet 124, and this region of the ampoule body 114 forms a skin contact surface 126 when used as intended. Compared to other embodiments, the rounded form of the skin contact surface 126 at the distant end of the ampoule 112 results in a significantly enlarged and also continuous skin contact surface 126, thereby achieving a good seal already at relatively small pressures. The elimination of edges in the region of the skin contact surface 126 also reduces pressure-induced pain.

Lastly, the shape provides a wide tolerance range of application angles of the ampoule 112 on the skin surface 126, while almost completely eliminating the danger of wet shots during injection. Wet shots are to be understood as injections where the injected fluid does not penetrate the skin at all or penetrates the skin only partially, and instead flows across the skin surface.

The injection device 110 also includes a first coupling element 128 which is arranged on/at the ampoule body 114. The first coupling element 118 is implemented as a bead extending around one half of the circumference and engages in the intended configuration with a complementary second coupling element 162 of the needle attachment 150, as will be described in more detail below. The two coupling elements 128, 162 are parts of a coupling assembly which is implemented as a bayonet lock, as depicted in FIGS. 1a to 1d.

The needle attachment 150 can be divided into a cannula part 152 and an adapter part 154.

The cannula part 152 includes a needle 156 which may be, for example, an injection needle. In the present example, the needle 156 is provided with a protective cap 158.

The adapter part 154 defines a receiving region 160 for the distal end of the actual body 114; the receiving region 160 is configured to seal the outlet 124 around the fluid when properly biased against the ampoule body 114. To provide a tight fit, the receiving surface 160 may have exactly the same dimensions as the distal end of the ampoule body 114, or the receiving region 160 of the adapter part 154 may be coated with a somewhat elastic material, wherein the dimensions of the receiving region 160 are slightly smaller than would otherwise be required for the distal end of the ampoule body 114. When the ampoule body 114 is inserted into the receiving region 160 of the adapter part 154, the elastic coating or the elastic material is compressed in the region 160, thereby adequately sealing the region against the fluid.

The adapter part 154 also includes the second coupling element 162. In the present example, the coupling element 162 is a recess for a bayonet lock disposed along the circumference of the adapter part 154 with dimensions that match those of the complementary first coupling element 128 on the ampoule body 114.

FIG. 2 shows in a cross-sectional view an adapter part 254 which can form the basis for a two-part needle attachment. The adapter part 254 is constructed similar to the adapter part 154 described above with reference to FIGS. 1a to 1c, and reference is made here to the respective description. However, the adapter part 254 is implemented as a separate part from the cannula part, with its distal end being implemented as a Luer connection 264, to which conventional needle attachments with needle can be attached.

LIST OF REFERENCE SYMBOLS 110 injection device
112 ampoule
114 ampoule body
116 chamber
118 ampoule piston
120 end section
122 pressure surface for the thumb
124 outlet
126 skin contact surface
128 coupling element
150 needle attachment
152 cannula part
154 adapter part
156 needle
158 protective cap
160 receiving region
162 coupling element
254 adapter part
264 Luer connection

The invention claimed is:

1. System for injecting a fluid through or into the human skin, optionally by needle-free injection or by injection with a needle, comprising
   (i) an injection device comprising
      an ampoule with an ampoule body forming a chamber for receiving the fluid to be injected;
      an ampoule piston which is axially movable and sealingly guided in the chamber;
      an outlet of the ampoule located at a distant end of the ampoule for the fluid to be injected, wherein the outlet of the ampoule is in direct fluid communication with the chamber of the ampoule, wherein the ampoule is rounded in the region of the outlet of the ampoule and the rounded region of the ampoule forms a skin contact surface for the needle-less injection through or into the human skin; and
      at least one first coupling element of a coupling device which is arranged at the distal end of the ampoule on the ampoule body and configured for sealingly and reversibly attaching a needle attachment, and
   (ii) a needle attachment with
      a cannula part comprising a needle; and
      an adapter part proximally connected to the cannula part, wherein the adapter part has at least one second coupling element of the coupling device, the coupling device configured for sealing and reversible attachment on the ampoule of the injection device,
   wherein
   the needle attachment is constructed in two parts, wherein the needle attachment can be reversibly disassembled into the cannula part and the adapter part.

2. System according to claim 1, wherein the adapter part comprises a Luer-connection for the cannula part.

3. System according to claim 1, wherein the skin contact surface has an essentially edge-free contour.

4. System according to claim 1, wherein the skin contact surface has a convex contour.

* * * * *